(12) United States Patent
Lau et al.

(10) Patent No.: US 11,903,549 B2
(45) Date of Patent: Feb. 20, 2024

(54) APPARATUS AND METHODS FOR SAFELY COLLECTING AND DISPOSING OF SHARPS WASTE

(71) Applicants: Robyn Lynn Lau, Grass Valley, CA (US); Wayne David Gregory Lau, Grass Valley, CA (US)

(72) Inventors: Robyn Lynn Lau, Grass Valley, CA (US); Wayne David Gregory Lau, Grass Valley, CA (US)

( * ) Notice: Subject to any disclaimer, the term of this patent is extended or adjusted under 35 U.S.C. 154(b) by 360 days.

(21) Appl. No.: 16/882,015

(22) Filed: May 22, 2020

(65) Prior Publication Data

US 2020/0367709 A1    Nov. 26, 2020

Related U.S. Application Data

(60) Provisional application No. 62/852,226, filed on May 23, 2019.

(51) Int. Cl.
*A47L 7/00* (2006.01)
*A47L 5/22* (2006.01)
*A47L 9/14* (2006.01)

(52) U.S. Cl.
CPC ............... *A47L 7/0071* (2013.01); *A47L 5/22* (2013.01); *A47L 9/1409* (2013.01)

(58) Field of Classification Search
None
See application file for complete search history.

(56) References Cited

U.S. PATENT DOCUMENTS

| 7,257,858 B2 | 8/2007 | Palazzolo |
| 7,962,996 B1 | 6/2011 | Mondello |
| 2017/0079489 A1 * | 3/2017 | Dimbylow ................ A47L 5/28 |

FOREIGN PATENT DOCUMENTS

WO    WO-2019030478 A1 *   2/2019    ............. A47L 5/225

* cited by examiner

*Primary Examiner* — Natasha N Campbell
*Assistant Examiner* — Pradhuman Parihar
(74) *Attorney, Agent, or Firm* — Jacob W Neu; Lucas R. Yordy; Bradley Arant Boult Cummings LLP (57) ABSTRACT

A vacuuming apparatus for collecting and disposing of sharps waste is disclosed. The sharps waste may include a used hypodermic needle. The vacuuming apparatus includes a passageway including a sidewall defining an interior chamber. The passageway includes an open suction end and an open nozzle end dimensioned to receive the sharps waste. The vacuuming apparatus includes a discharge port located at the suction end and in gaseous communication with a container, such as a used sharps container. The vacuuming apparatus includes a fan, that when operated, is configured to move air from the open nozzle end to the suction end and into the container such that the sharps waste may be moved in an airstream from a surface proximate to the open nozzle end into the container.

14 Claims, 12 Drawing Sheets

APPARATUS AND METHODS FOR SAFELY COLLECTING AND DISPOSING OF SHARPS WASTE

CROSS-REFERENCE TO RELATED APPLICATION

This application claims the benefit of U.S. Provisional Patent Application No. 62/852,226, filed May 23, 2019, which is incorporated by reference herein in its entirety.

TECHNICAL FIELD

The present disclosure relates to apparatus and methods for collecting and disposing of used sharps waste. More specifically, the disclosure is directed towards apparatus for safely and efficiently vacuuming used sharps waste with minimal, or no, direct handling of the sharps waste.

BACKGROUND OF INVENTION

Improperly discarded sharps waste are massive worldwide health, environmental, and quality of life issues. While improperly disposed of sharps waste has always presented a community risk, the recent rise in injectable illegal drug abuse (e.g., heroin) has magnified the problem. In 2019, the Boston Globe reported that Boston alone picks up 14,000 improperly discarded used needles each week. Meanwhile, in 2018, the BBC reported that improperly discarded needs and syringes were being removed up to 50 times per day from play areas and car parks. Unfortunately, these are not isolated reports, and improperly discarded sharps waste is a worldwide problem in public and common places, such as parks, along sidewalks, on benches and seats, and even in public transit stations and vehicles.

In addition to being unsightly and an environmental pollutant, improperly disposed sharps waste presents a health risk, as used sharps have the possibility of transmitting infectious disease and introducing harmful foreign agents, such as traces of drugs or environmental pollutants, through sticks with the sharps. Moreover, sharps waste presents a puncture hazard to those who encounter it.

However, despite the widespread and increased prevalence of improperly discarded sharps waste, current methods and apparatus for collection are inadequate. Indeed, a commonly recommended method for disposing of impurely discarded sharps waste is to use tongs, or a scooper, and to pick up the discarded sharps waste and transfer the sharps waste into a proper sharps container. However, because of the small nature, and frequently elongated shape, of sharps, such a transfer is cumbersome and often results in the collector accidentally sticking themselves. Moreover, many do not follow even this practice, instead directly picking up (whether with bare hands or covered hands, such as a glove) the sharps waste for disposal.

Thus, a need exists for better apparatus and methods for disposing of improperly discarded sharps waste.

BRIEF SUMMARY

In one aspect, a vacuuming apparatus for collecting and disposing of sharps waste is disclosed. The sharps waste may comprise a used hypodermic needle. The vacuuming apparatus includes a passageway including a sidewall defining an interior chamber. The passageway includes a suction end and an open nozzle end dimensioned to receive a sharps waste.

The vacuuming apparatus includes a fan configured to move air from the open nozzle end to the suction end. The fan may be selectively powered by a motor. The fan may be configured to move the air with a sufficient volume and velocity to collect a sharps waste from a surface. The air volume of the air at the nozzle end may be between 50 cubic feet per minute (cfm) and 1500 cfm, and the air velocity of the air at the nozzle end may be between 50 miles per hour (mph) and 500 mph.

The vacuuming apparatus includes a discharge port in gaseous communication with the interior chamber and between the suction end and the open nozzle end. A container, such as a rigid sharps container, is disposed on the discharge port. The container may be releasably secured on the discharge port. The container may be constructed of a puncture-proof material, such as high-density polyethylene or a metal. The container may include a bottom and side walls and be leak-proof from the bottom and the side walls. The passageway 12 may comprise a rigid filter configured to direct the sharps waste into the container. A discharge body may be disposed between the fan and the open nozzle end. The discharge port may be disposed on the discharge body.

The vacuuming apparatus is configured so that when the fan moves air from the open nozzle end to the suction end, a sharps waste is drawn through the open nozzle end through at least a portion of the interior chamber, through the discharge portion, and into the container.

The vacuuming apparatus may include an exhaust gaseous communication with the fan and configured to discharge air moved through the discharge port and the interior chamber. The passageway may extend from the open nozzle end to the suction end in a first axis. The discharge port may extend generally orthogonally from the first axis.

In another aspect, a method for sequestering sharps waste is disclosed. The method includes providing a vacuuming apparatus. The vacuuming apparatus includes a passageway including a sidewall defining an interior chamber, the passageway including a suction end and an open nozzle end dimensioned to receive a sharps waste. The vacuuming apparatus includes a fan configured to move air from the open nozzle end to the suction end. The vacuuming apparatus includes a discharge port disposed on the sidewall between the suction end and the open nozzle end. The vacuuming apparatus includes a container disposed on the discharge port.

The method includes powering the motor to move air from the open nozzle end to the suction end. The method includes positioning the open nozzle end proximate to the sharps waste to sequester the sharps waste. The sequestered sharps waste may pass through the open nozzle end, at least partially through the interior chamber and the discharge port, and into the container. The method may include releasing the container from the discharge port. The released container may be sealed. The sharps waste may be collected from a surface.

In yet another aspect, a discharge apparatus for collecting sharps waste is disclosed. The discharge apparatus comprises a rigid body including a nozzle side, a suction side disposed oppositely on the rigid body from the nozzle side, and a container side disposed orthogonally from the nozzle side and the fan side. The nozzle side is configured to securely and releasably receive a nozzle. The fan side is configured to securely and releasably receive a suction tube, such as on a fan housing. The container side is configured to securely and releasably receive a container.

The discharge apparatus includes a cavity that extends from the nozzle side to the fan side and extends to the container side. The cavity may be defined by cavity sidewalls that extend downwardly from the nozzle side to the container side. The discharge apparatus may be configured so that when an airstream containing a sharps waste passes through the cavity, the sharps waste is moved from the nozzle end toward the fan end and collected in the container.

BRIEF DESCRIPTION OF DRAWINGS

It should be noted that identical features in different drawings are shown with the same reference numeral.

DETAILED DESCRIPTION

Reference now will be made in detail to the embodiments of the present disclosure. It will be apparent to those of ordinary skill in the art that various modifications and variations can be made to the teachings of the present disclosure without departing from the scope of the disclosure. For instance, features illustrated or described as part of one embodiment can be used with another embodiment to yield a further embodiment.

Thus, it is intended that the present disclosure covers such modifications and variations that come within the scope of the appended claims and their equivalents. Other objects, features, and aspects of the present disclosure are disclosed in or are apparent from the following description. It is to be understood by one of ordinary skill in the art that the present disclosure is a description of exemplary embodiments only and is not intended as limiting the broader aspects of the present disclosure.

For the sake of clarity, not all reference numerals are necessarily present in each drawing Figure. In addition, positional terms such as "upper," "lower," "side," "top," "bottom," "vertical," "horizontal," etc. refer to the apparatus when in the orientation shown in the drawings. The skilled artisan will recognize that the apparatus can assume different orientations when in use.

Figure 1:
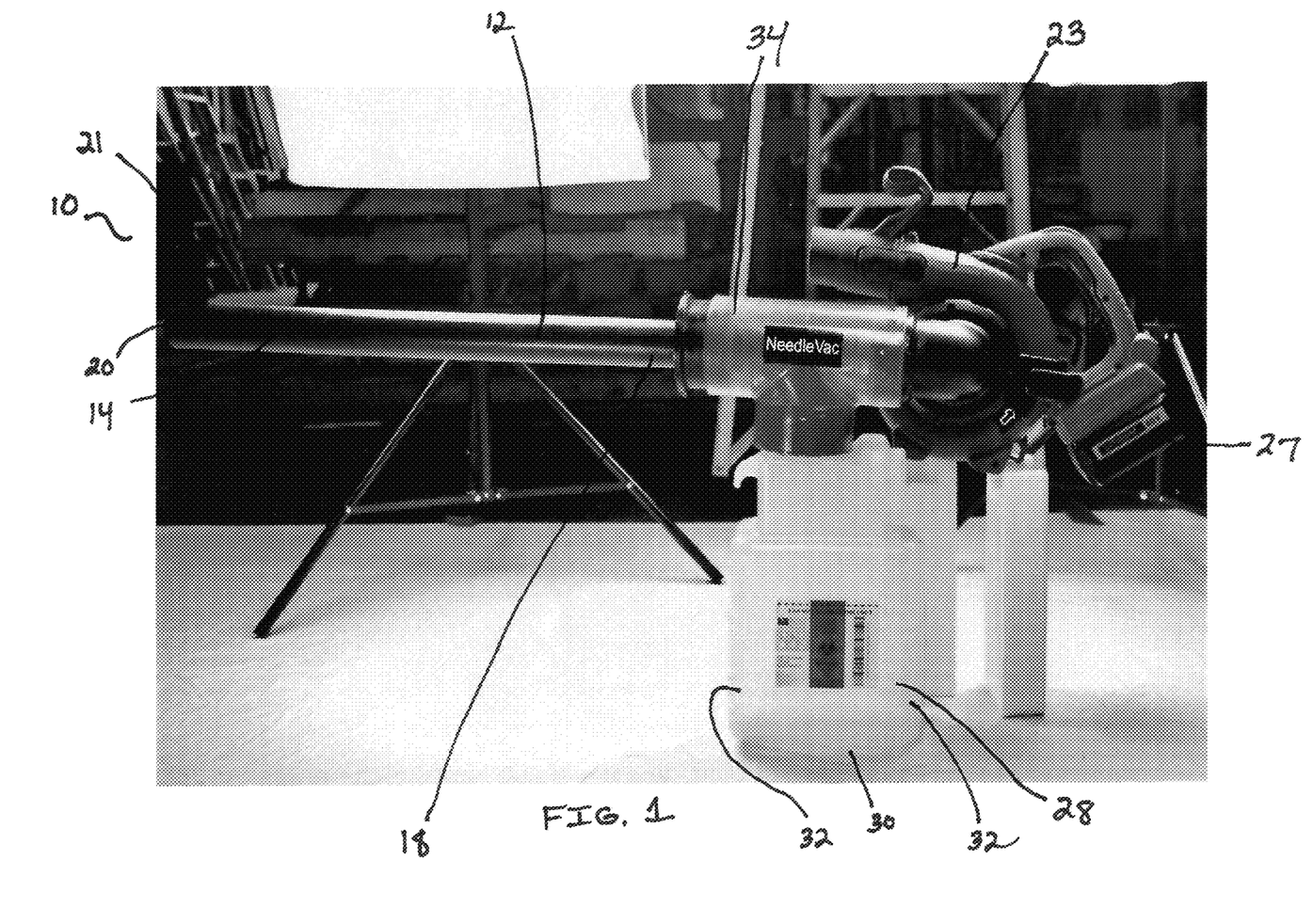
FIG. 1 shows a left side elevation view of a vacuuming apparatus according to an embodiment.
Figure 2:
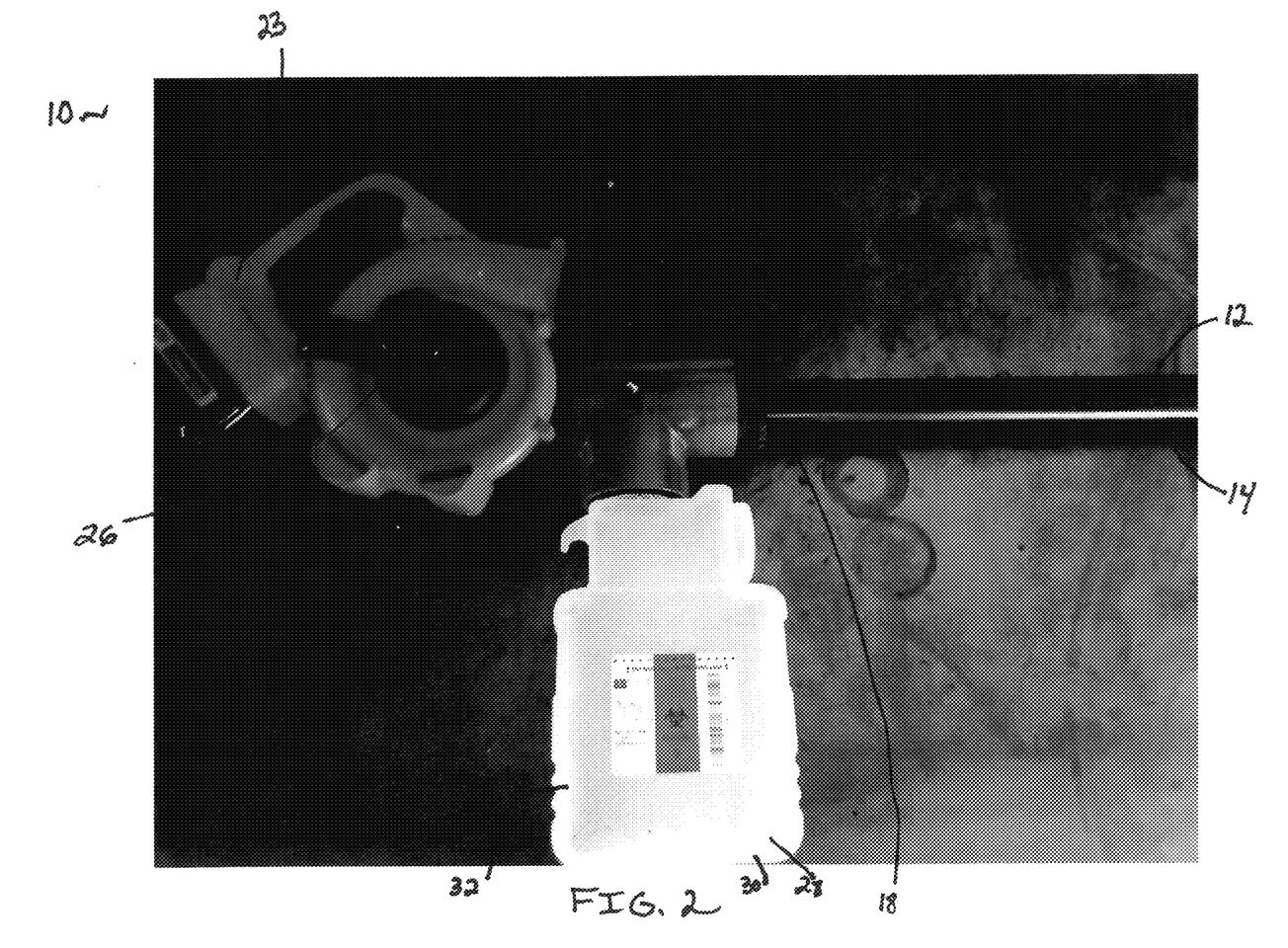
FIG. 2 shows a right side view of the vacuuming apparatus of FIG. 1.
Figure 3:
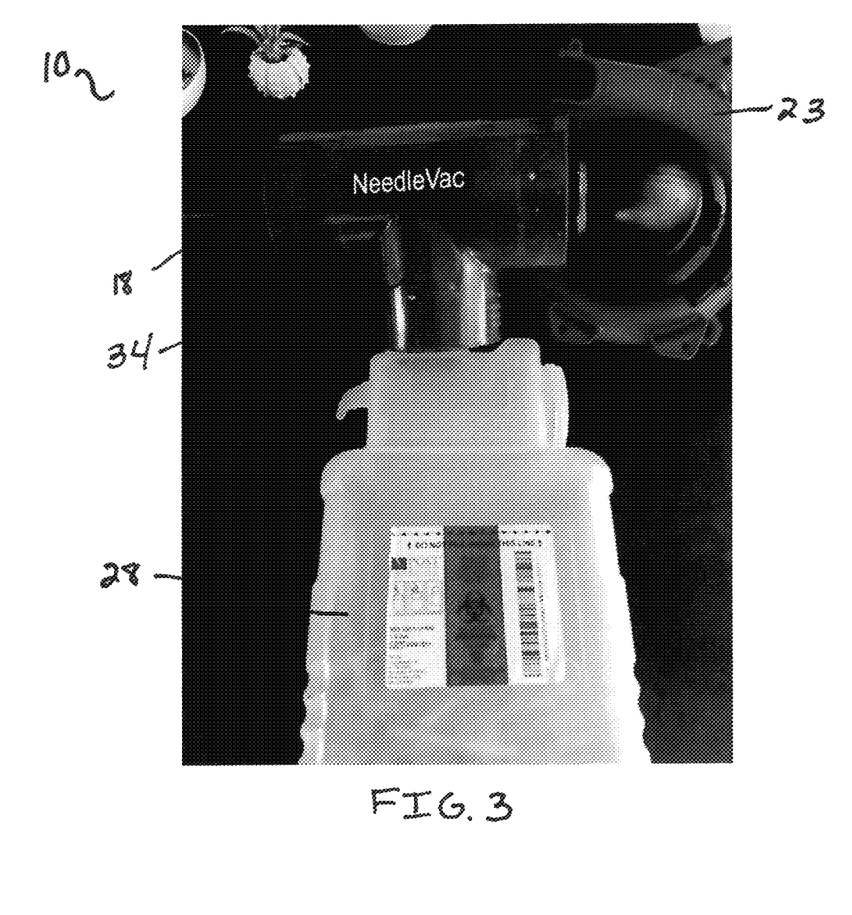
FIG. 3 shows a close-up view of the container and discharge body of the vacuuming apparatus of FIG. 1.
Figure 4:
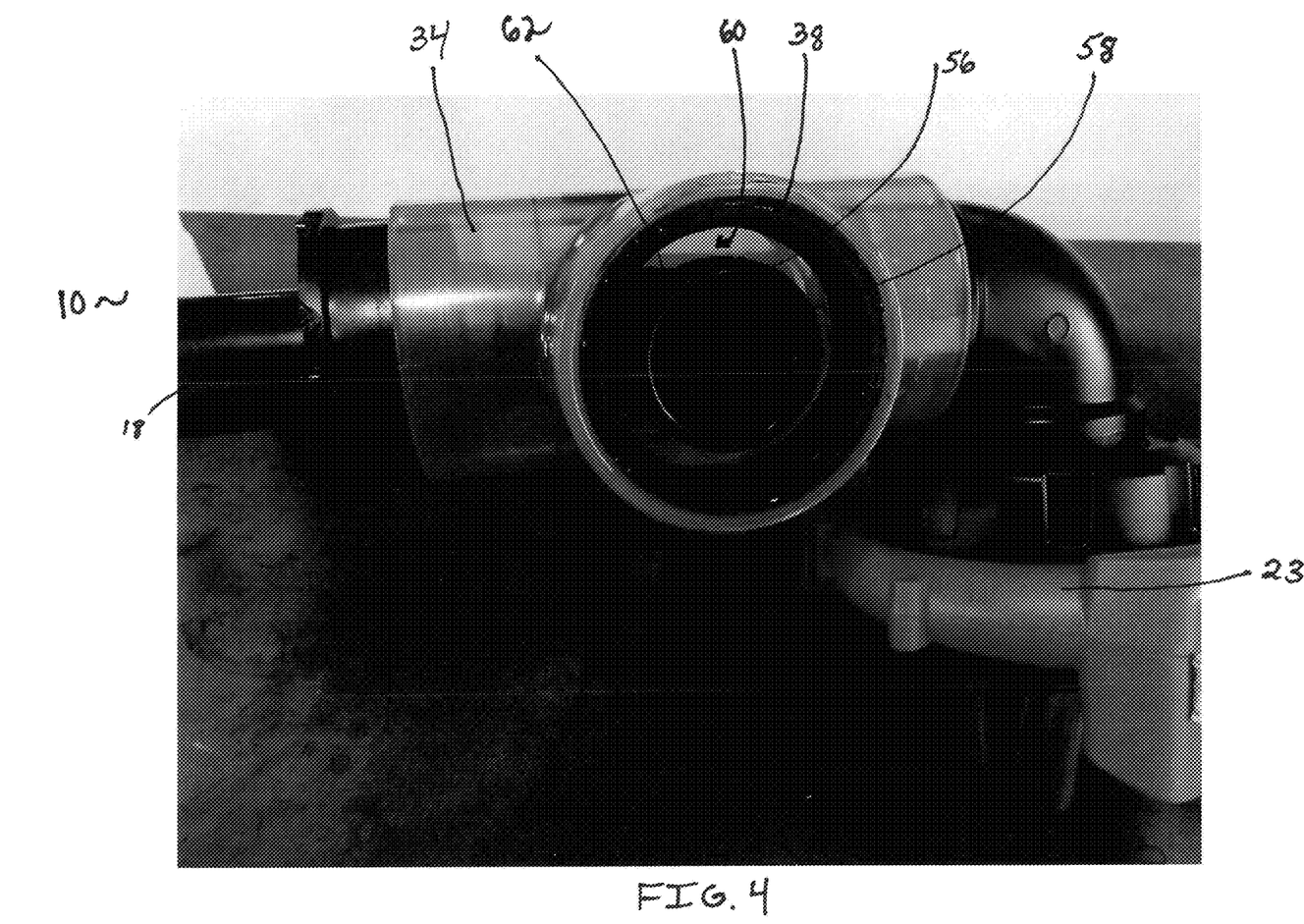
FIG. 4 shows a bottom close-up view of a discharge body without a container.
Figure 5:
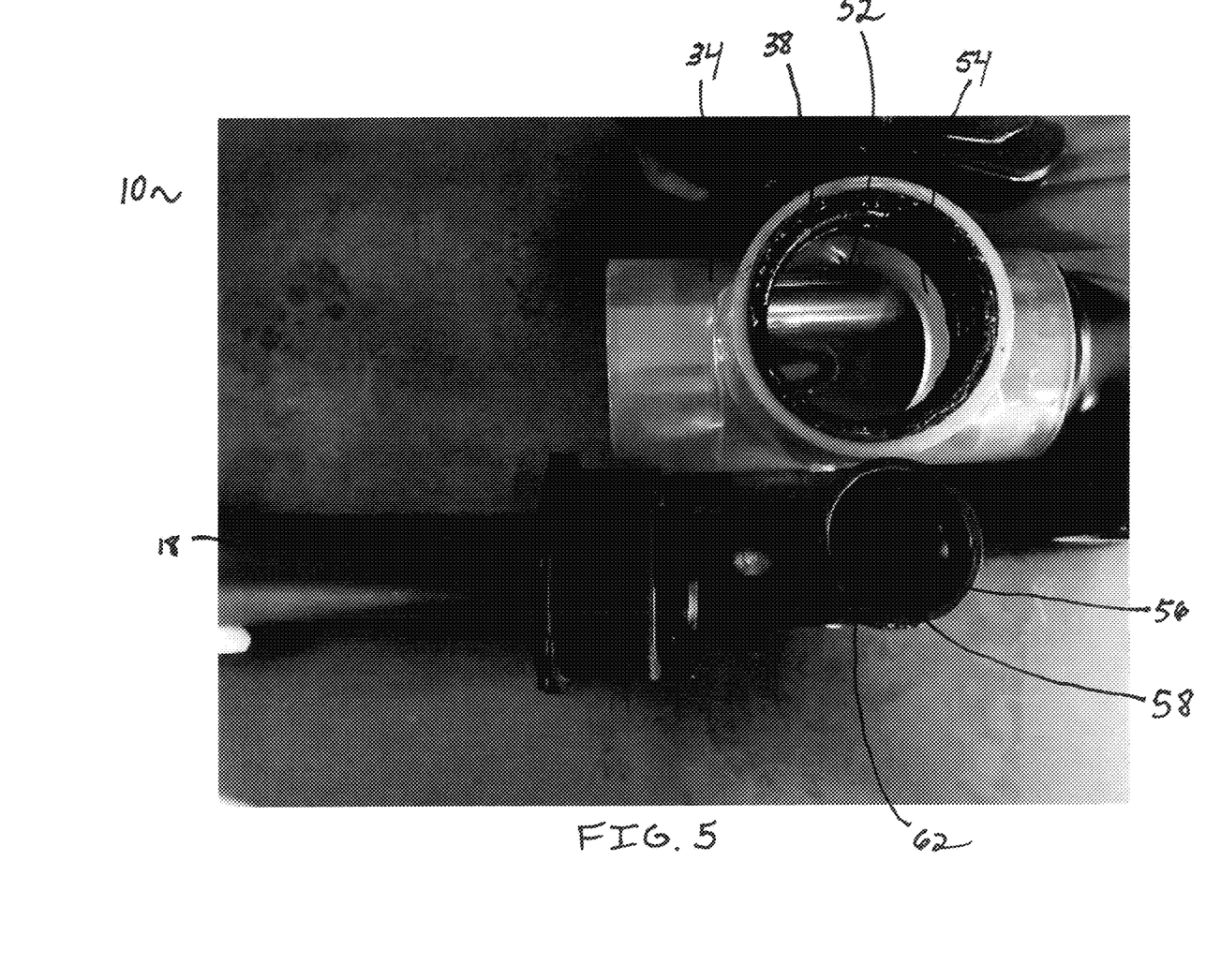
FIG. 5 shows a bottom close-up view of a discharge body without a container and with a detached passageway.
Figure 6:
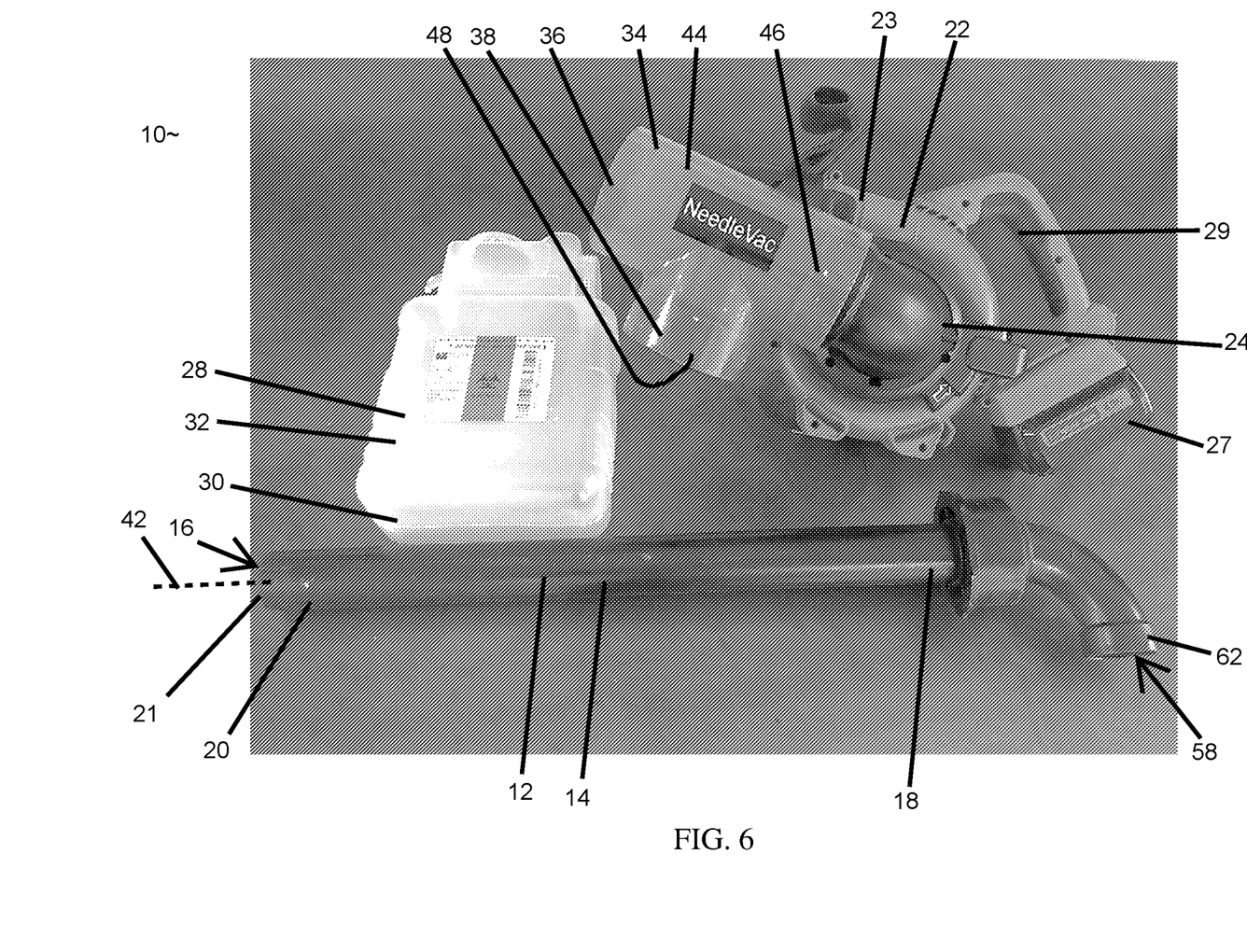
FIG. 6 illustrates a partial cutaway view of a vacuuming apparatus having a detached container a detached passageway.
Figure 7:
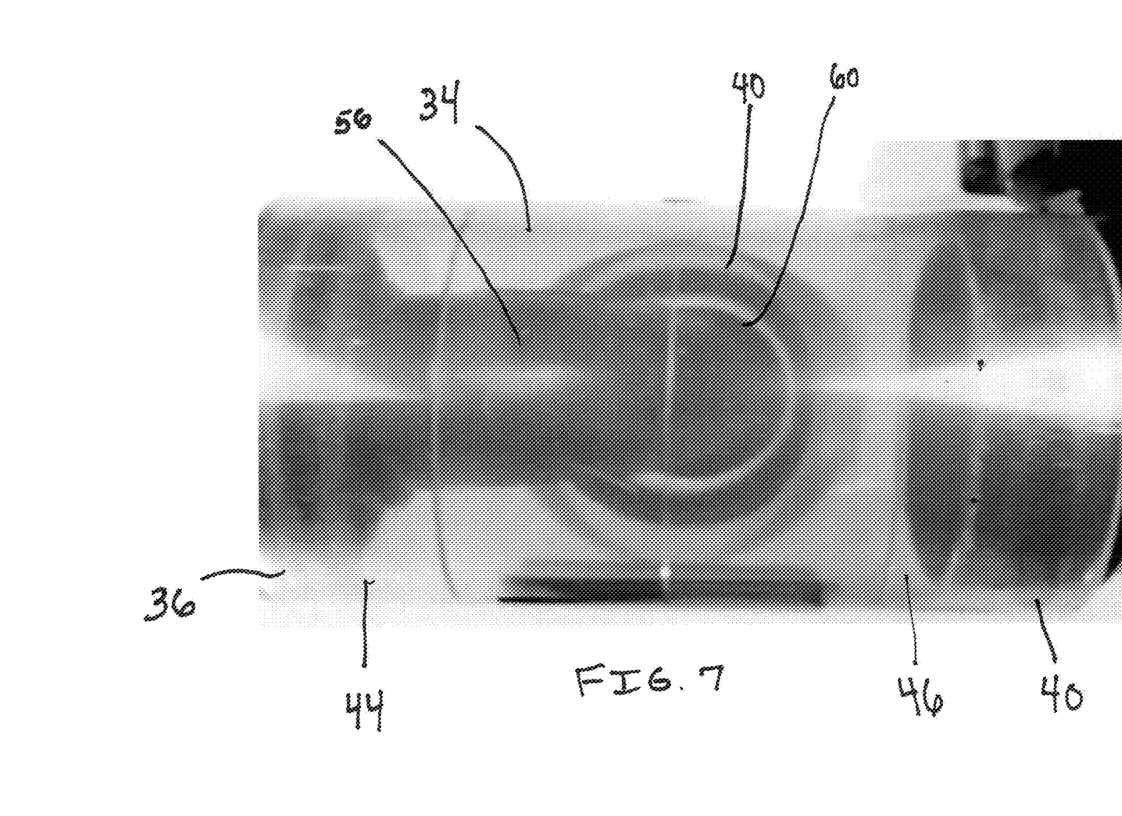
FIG. 7 shows a top view of a discharge body and a downwardly extending portion.
Figure 8:
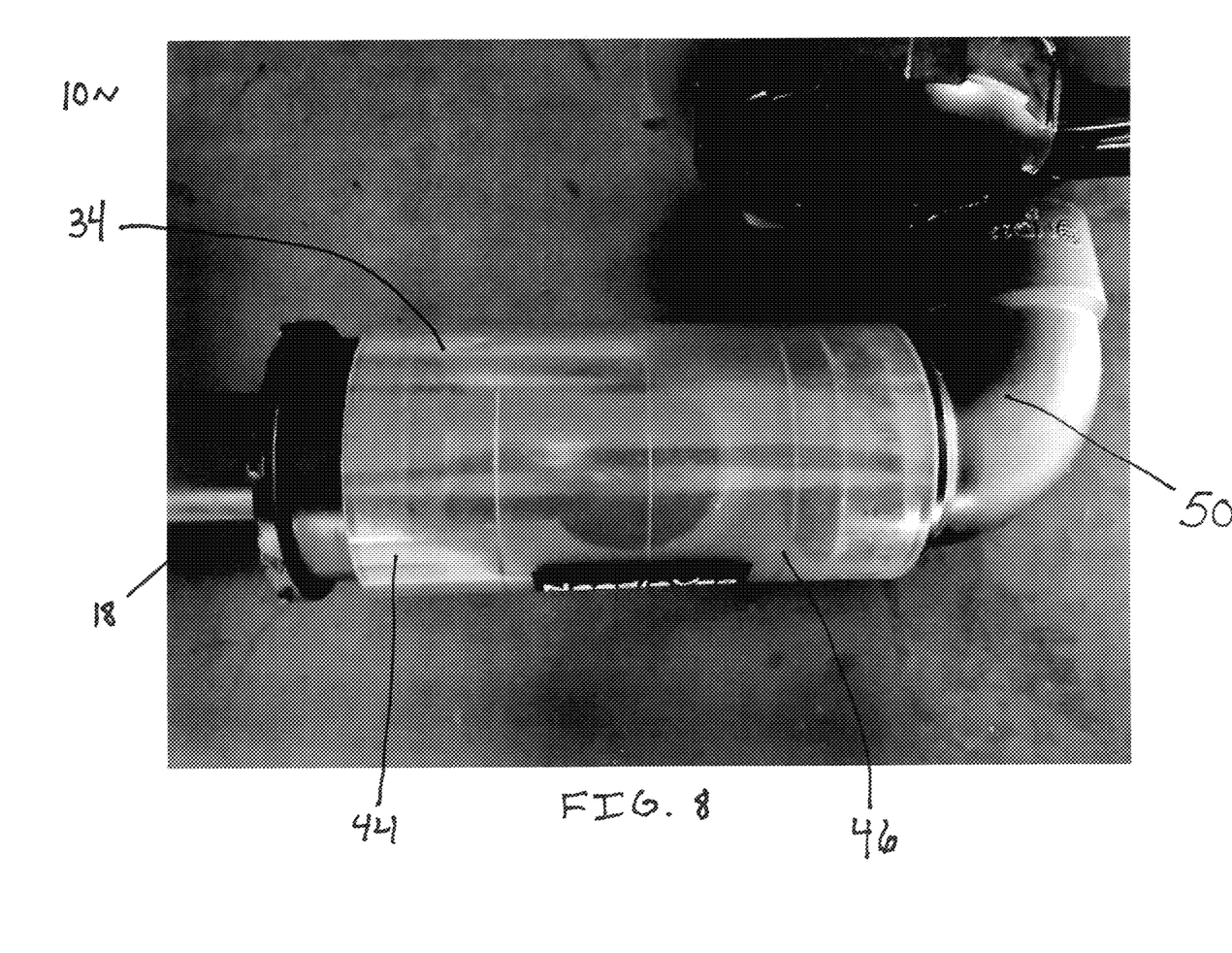
FIG. 8 shows a top view of a discharge body without the downwardly extending portion.
Figure 9:
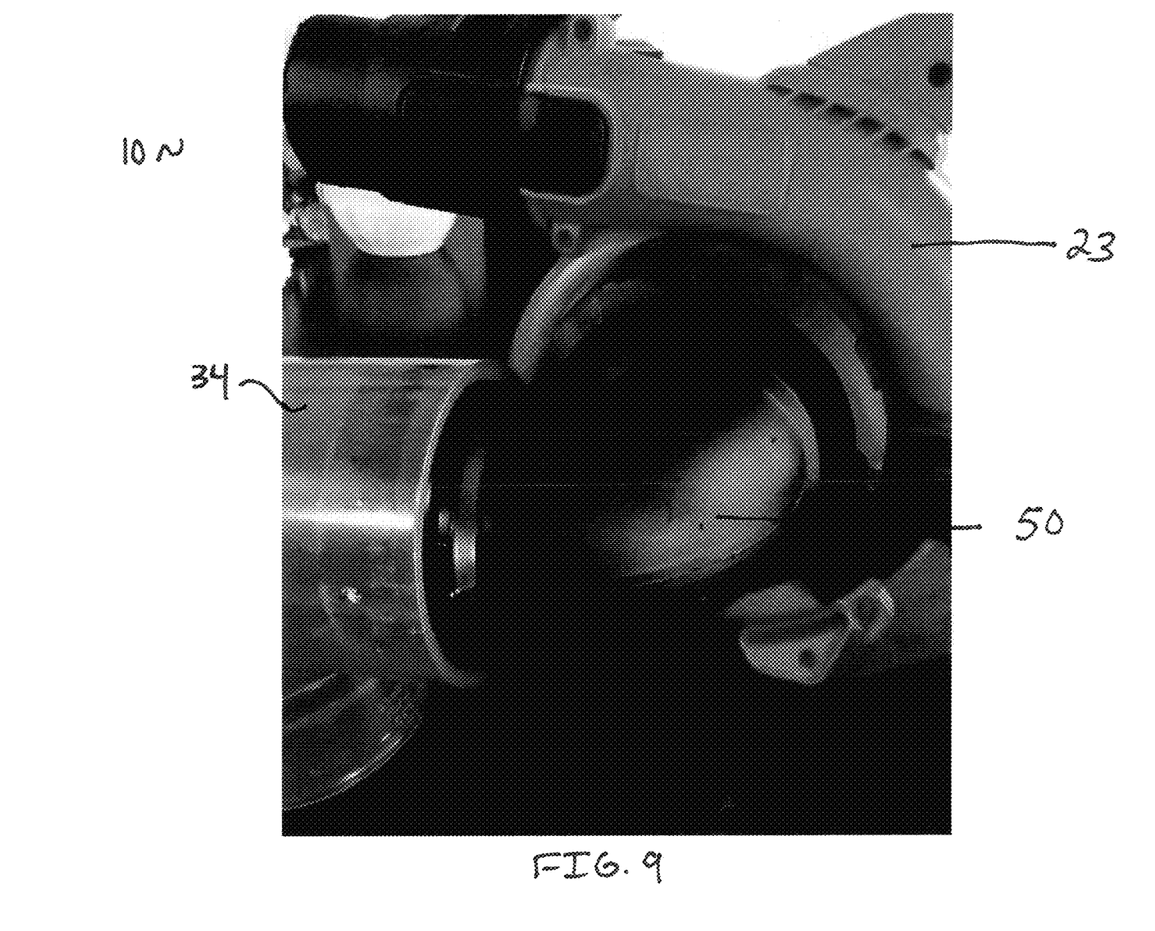
FIG. 9 shows a close-up view of a fan housing and a suction tube.
Figure 10:
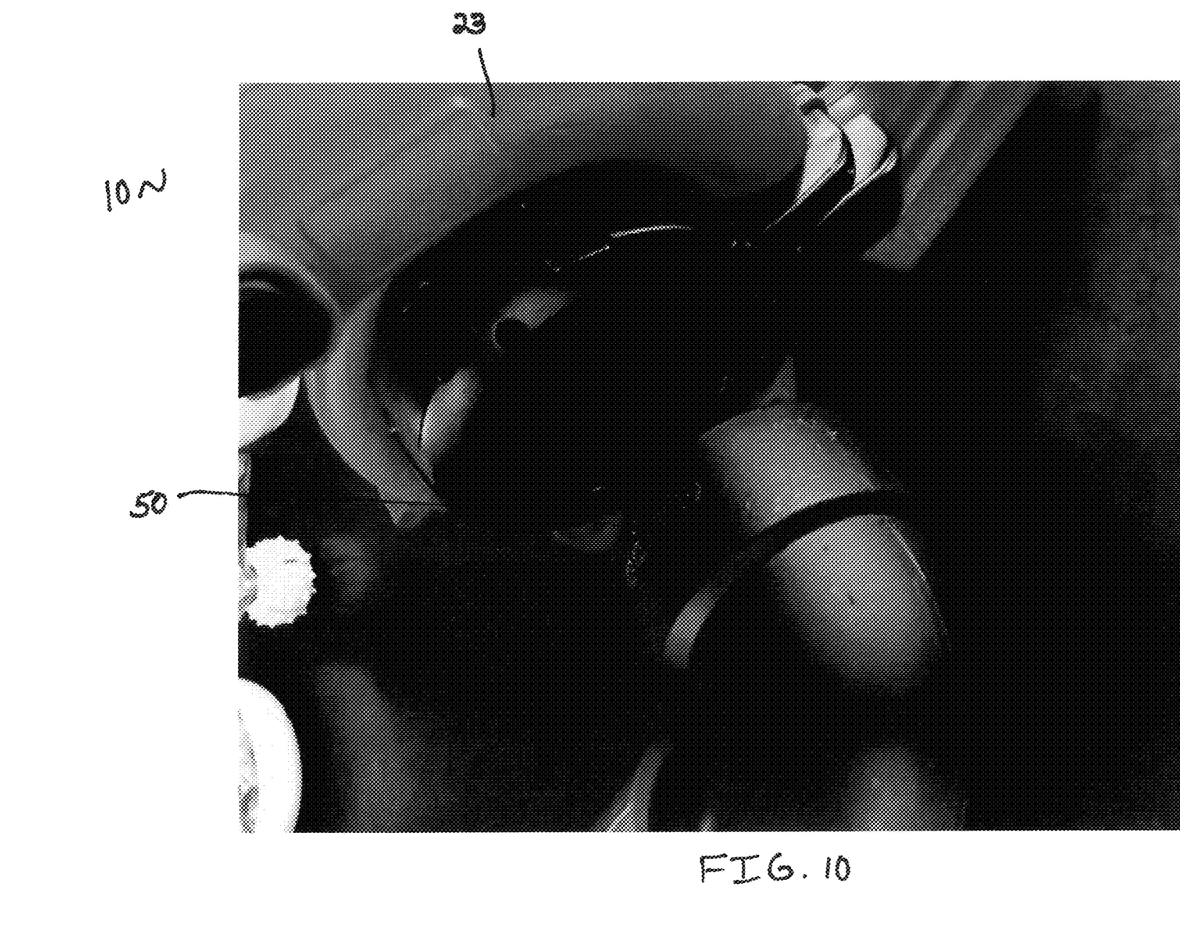
FIG. 10 shows another close-up view of a fan housing and a suction tube.
Figure 11:
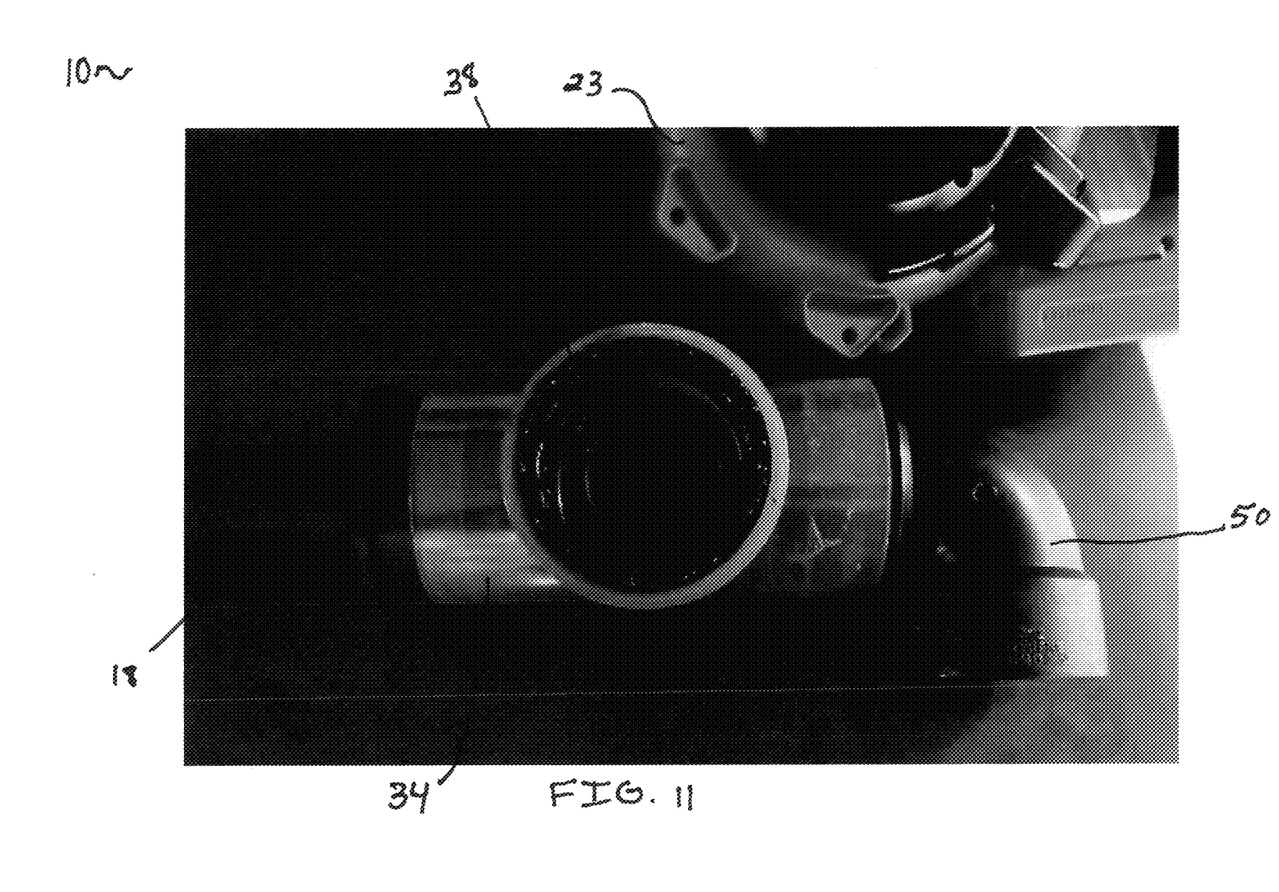
FIG. 11 shows a bottom view of a discharge body without the downwardly extending portion.
Figure 12A:
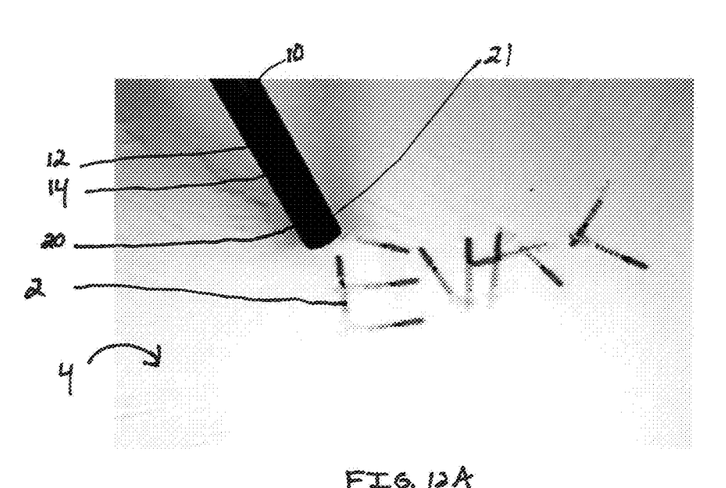
FIGS. 12A and 12B show an embodiment of the vacuuming apparatus collecting sharps waste from a surface.
Figure 12B:
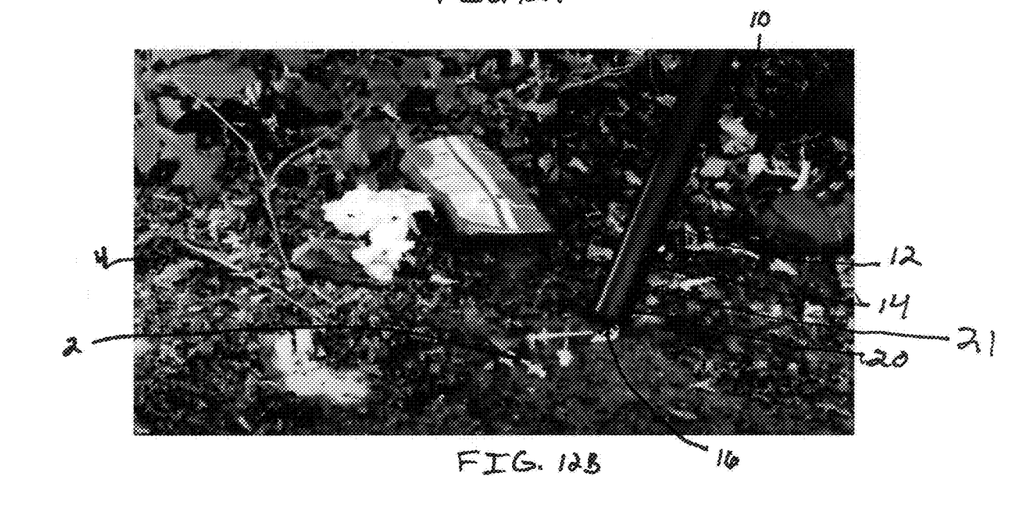

Referring to FIGS. 1-12B, a vacuuming apparatus 10 for collecting and disposing of sharps waste 2 has been developed. The sharps waste 2 may be one or more used needles or sharps, such as a used hypodermic needle. However, the sharps waste 2 need not puncture the skin to be considered "used." Rather, any discarded sharp may be considered sharps waste 2. The sharps waste 2 may be disposed on any surface 4, such as the ground, a table, a seating area, or a floor (whether as a structure or in a public transit vehicle).

The vacuuming apparatus 10 includes a passageway 12 for moving air. The passageway 12 includes a sidewall 14 that defines an interior chamber 16 within which for the moving air to travel (as well as objects, such as the sharps waste 2, carried in the moving air). The passageway 12 may be constructed of any suitable material, such as a polymer (e.g., high-density polyethylene) or metal (e.g., aluminum or steel). The passageway 12 may be rigid or flexible. The passageway 12 may be dimensioned such that the sharps waste 2 may pass, at least partially, through the passageway 12.

The passageway 12 may comprise an open suction end 18. The suction end 18 may be configured to be cooperatively received in a device that generates suction, such as a leaf vacuum or household floor vacuum. The passageway 12 may comprise an open nozzle end 20 disposed on the passageway 12 oppositely from the suction end 18. The open nozzle end 20 may be dimensioned to receive the sharps waste 2. The open nozzle end 20 may comprise a nozzle 21 configured to facilitate the collection of the sharps waste 2.

The suction end 18 may be configured to cooperatively interface with (such as be received in or on) a discharge port 26. In some embodiments of the apparatus 10, the suction end 18 may be dimensioned and configured such that the sharps waste 2 can freely pass through it. In other embodiments, the suction end 18 may be dimensioned and configured such that sharps waste 2 cannot freely pass the suction end 18, depending on what other structures block potential contact with a fan 22 of the apparatus 10 for moving the air through the passageway 12.

The fan 22 may be configured to move air from the open nozzle end 20 to the suction end 18, thus creating "suction" at the open nozzle end for collecting the sharps waste 2. Any suitable fan may be used for the fan 22, such as a centrifugal fan. The fan 22 may be selectively rotated (i.e., powered) by a motor 24. The motor 24 may rotate the fan 22 selectively, such as low, medium, and high speeds, or at adjustably variable speeds. The motor may be powered by any suitable means, including electricity (whether alternating or direct current), a rechargeable battery 27 (such as lithium-ion), or a fuel (such as gasoline or a gasoline-oil mixture). The fan 22 operatively connected to the motor 27, which is selected operated with trigger 29, is illustrated schematically in a partial cut away view in FIG. 6.

The fan 22 may be configured to move the air with a sufficient volume and velocity to collect the sharps waste 2 from the surface 4. The air volume of the air at the open nozzle end 20 may be at least 50 cubic feet per minute (cfm), at least 100 cfm, at least 150 cfm, at least 200 cfm, at least 250 cfm, at least 300 cfm, at least 500 cfm, at least 750 cfm, at least 1000 cfm, at least 1500 cfm, or any subrange or subvalue thereof. The air velocity the air at the open nozzle end 20 may be at least 50 miles per hour (mph), 75 mph, 100 mph, 150 mph, 200 mph, 250 mph, 300 mph, at least 500 mph, or any subrange or subvalue thereof. The fan 22 may be contained in a fan housing 23.

The vacuuming apparatus 10 may include a discharge port 26 in gaseous communication with the interior chamber 16. The discharge port 26 may provide an outlet for the sharps waste 2 to be separated from the interior chamber 16 and collected. A container 28 may be disposed on, such as releasably secured on, the discharge port 26. The container 28 may be any suitable container for the sharps waste 2. For example, the container 28 may be constructed of a puncture-proof material, such as high-density polyethylene or metal. The container 28 may be rigid or flexible (e.g., a constructed of a high tensile strength fabric). The container 28 may be a rigid sharps container, such as typically used medical sharps waste containers. The container 28 may comprise a bottom 30 and side walls 32 extending upwardly from the bottom 30. The container 28 may be leak-proof from the bottom 30 and the side walls 32 such that no leakage occurs of bodily fluids or other potentially dangerous substances. The container 28 may be sealable or resealable when released from the apparatus 10 such that its contents (e.g., the sharps waste 2) are safely secured within.

The vacuuming apparatus 10 may comprise a discharge body 34 (also referred to as a discharge apparatus). The discharge body 34 may be disposed between the fan 22 and the open nozzle end 20. The discharge body 34 may be integrally formed with the passageway 12 or formed separately. The discharge body 34 may provide an interface between the passageway 12, the container 28, and the fan housing 23. The discharge port 26 may be disposed on the discharge body 34. Each of the passageway 12, the container 28, and the fan housing 23 may be configured to be releasably secured with a corresponding passageway interface 36, a container interface 38, and a fan housing interface 40, such as via cooperative threading, snaps, a friction fit, or any other suitable fastener.

The direction of airflow from the open nozzle end 20 and the suction end 18 may define a first axis 42 (which may also correspond to the lengthwise direction along which the passageway 12 extends). The passageway interface 36 may be disposed on a nozzle side 44 of the discharge body 34. The fan housing interface 40 may be disposed on a fan side 46 of the discharge body 34. The nozzle side 44 and the fan side 46 may both be disposed on the first axis 42. The container interface 38 may be disposed on a container side 48 of the discharge body 34. The container interface 38 may be positioned on the discharge body 34 orthogonally from the first axis 42. Advantageously, the discharge body 34 may allow parts of the apparatus to be replaced when worn out (e.g., the passageway 12 or the fan 22 in the fan housing 23) or full (e.g., the container 28). The interfaces 36, 38, 40 may be open such as to freely permit airflow. In some embodiments, the fan housing interface 40 may be configured to receive a suction tube 50, such as on the fan housing 23 or a household vacuum (not shown) to communicate air movement from the fan 22.

The discharge body 34 may include a cavity 52 defined by cavity sidewalls 54 for moving air within and through the discharge body 34 and also for receiving a suction end 18 of the passageway 12. The suction end 18 of the passageway 12 may comprise a downwardly extending portion 56. In embodiments of the apparatus 10 where the discharge body 34 and the passageway 12 are releasable from one another, when the discharge body 34 and the passageway 12 are joined, the downwardly extending portion 56 extends from the nozzle side 44 to the container side 48. The discharge port 26 may be disposed directly on the passageway 12 or on the discharge body 34.

The downwardly extending portion 56 may comprise a narrowed cavity 58 that is narrower (e.g., smaller in diameter) than the interior chamber 16 of the passageway 12. A gap 60 may extend around the downwardly extending portion 56 positioned at a container end 62 of the downwardly extending portion 56. The gap 60 may be dimensioned such that the sharps waste 2 may not pass through (fully or substantially) the gap 60. Advantageously, the narrowed downwardly extending portion 56 and the gap 60 allow air moved by the fan to pass from the interior chamber 16, through the downwardly extending portion 56 and into the container 28, carrying the sharps waste into the container 28. Moved air can escape the container 28 through the gap 60, through the cavity 52 of the discharge body 34, and to the fan side 46 (and then fan 22 and to an exhaust 64), thus allowing the fan 22 to maintain a continuous movement of air from the suction end 18 and through the apparatus 10.

While the air can pass through the gap 60, the gap 60 is dimensioned such that the sharps waste 2 cannot substantially pass through the gap, thereby collecting the sharps waste 2 within the container. Thus, the discharge body 34 may be configured so that when air (i.e., an airstream generated by the fan 22) containing sharps waste 2 passes through the cavity 52, the sharps waste 2 is moved from the open nozzle end 20 toward the fan side 46 and collected into the container 28, thereby allowing for the safe and effective collection of the sharps waste 2 without direct human contact of the sharps waste 2. As used herein, "airstream" refers to a flow of air and anything the flow of air may contain (such as particulates, and in particular, the sharps waste 2).

The vacuuming apparatus 10 may include the exhaust 64 in gaseous communication with the fan 22. The exhaust 64 allows the fan 22 to discharge air drawn from the open nozzle end 20 and discharge air moved through the cavity 52, the discharge port 26, and the interior chamber 16 (among other features through which the fan 22 moves air).

The apparatus 10 and the discharge body 34 find use in, for example, methods for collecting (i.e., sequestering) and disposing of the sharps waste 2. The method may include providing the vacuuming apparatus 10. The method may include rotating the fan 22 (such as by selective power from the motor 24), to move air from the open nozzle end 20 to the suction end 18. The method may include positioning the open nozzle end 20 and the nozzle 21 proximate to the sharps waste 2. The open nozzle end 20 may be positioned at least as close as 0.5 centimeter (cm), 1 cm, 2 cm, 3, 4 cm, 5 cm, 7 cm, 10 cm, or any subrange or subvalue thereof, to the sharps waste 2 while air is passing through the open nozzle end 20. The sharps waste 2 may be collected from, for example, the surface 4 such as a floor or the outdoor ground. The sharps waste 2 may be drawn through the open nozzle end 18, at least partially through the interior chamber 16 and the discharge port 26, and into the container 28. The method may include releasing the container 28 from the discharge port 26. The released container 28 may be sealed. The released container 28, or the contents thereof, may be disposed of. An empty container 28 may replace the released container 28. Thus, the present methods are safe and effective to collect the sharps waste 2 without requiring that people directly contact (whether or not gloved) the sharps waste 2.

Although embodiments of the disclosure have been described using specific terms, devices, and methods, such description is for illustrative purposes only. The words are words of description rather than of limitation. It is to be understood that changes and variations may be made by those of ordinary skill in the art without departing from the spirit or scope of the present disclosure, which is set forth in the following claims. It is further noted that any range provided herein provides support and a basis for any subset within that range. Further embodiments of the disclosure contain combinations, or exclusions, of different embodiments described herein.

Thus, although there have been described embodiments of the present invention of a new and useful apparatus, it is not intended that such references be construed as limitations upon the scope of this invention except as set forth in the following claims.

What is claimed is:

1. A vacuuming apparatus for collecting and disposing of sharps waste, comprising:
   a passageway including a sidewall defining an interior chamber, the passageway including an open suction end having a downwardly extending portion with a container end, an open nozzle end dimensioned to receive a sharps waste, and a first axis defined by the direction between the open suction end and the open nozzle end;
   a fan housing including a fan configured to move air from the open nozzle end to the open suction end;
   a discharge body disposed between the fan and the open nozzle end, the discharge body including a cavity defined by cavity walls, a nozzle side with a passageway interface configured to secure to the open suction end of the passageway, a fan side having a fan housing interface configured to secure to the fan housing, and a container side including a discharge port in gaseous communication with the interior chamber and disposed on the sidewall between the open suction end and the open nozzle end, the discharge port including a container interface disposed orthogonal from the first axis and configured to secure to a container disposed on the discharge port;
   wherein, when the passageway and the discharge body are joined, the downwardly extending portion of the open suction end extends through the cavity of the discharge body from the nozzle side to the container side and a gap is formed between the container end of the downwardly facing portion and the container interface of the discharge port, the gap extending around the container end of the downwardly extending portion,
   wherein, when the fan moves air from the open nozzle end to the open suction end, the vacuum apparatus is configured to draw an airstream containing the sharps waste through the open nozzle end, through at least a portion of the interior chamber, through the downwardly extending portion, and into the container to deposit the sharps waste into the container, and
   wherein the vacuuming apparatus is configured to draw an airstream substantially free of sharps waste from the container through the gap, through the cavity of the discharge body, out of the fan side of the discharge body.

2. The vacuuming apparatus of claim 1, wherein the container is constructed of a puncture-proof material.

3. The vacuuming apparatus of claim 1, wherein the container has a bottom and side walls, and wherein the container is leak-proof from the bottom and the side walls.

4. The vacuuming apparatus of claim 1, wherein the container is a sharps waste container.

5. The vacuuming apparatus of claim 1, wherein the container interface of the discharge body is configured to releasably secure to the container.

6. The vacuuming apparatus of claim 1, wherein the passageway interface is configured to releasably secure to the passageway and the fan housing interface is configured to releasably secure to the fan housing.

7. The vacuuming apparatus of claim 1, further comprising a motor configured to selectively power the fan to move the air.

8. The vacuuming apparatus of claim 7, further comprising an exhaust in gaseous communication with the fan and configured to discharge air moved through the discharge port and the interior chamber.

9. The vacuuming apparatus of claim 1, wherein the air moved from the open nozzle end has a sufficient volume and velocity effective to collect the sharps waste from a surface.

10. The vacuuming apparatus of claim 1, wherein the fan is configured to generate movement of between 50 cfm and 1500 cfm of air at the open nozzle end.

11. The vacuuming apparatus of claim 1, wherein the fan is configured to generate air velocity of between 50 mph and 500 mph at the open nozzle end.

12. The vacuuming apparatus of claim 1, wherein the sharps waste comprises a used hypodermic needle.

13. The vacuuming apparatus of claim 1, wherein the downwardly extending portion comprises a narrowed cavity that is narrower than the interior chamber of the passageway.

14. The vacuuming apparatus of claim 1, wherein the gap is dimensioned such that sharps waste may not pass through the gap.

* * * * *